United States Patent [19]
Levy

[11] 4,024,241
[45] May 17, 1977

[54] NUCLEASE-RESISTANT HYDROPHILIC COMPLEX OF POLYRIBOINOSINIC-POLYRIBOCYTIDYLIC ACID

[75] Inventor: Hilton B. Levy, Bethesda, Md.

[73] Assignee: The United States of America as represented by the Secretary of Health, Education and Welfare, Washington, D.C.

[22] Filed: Sept. 4, 1975

[21] Appl. No.: 610,457

Related U.S. Application Data

[63] Continuation-in-part of Ser. No. 509,966, Sept. 27, 1974, Pat. No. 3,952,097.

[52] U.S. Cl. .......................... 424/85; 260/112.5 R; 424/177; 424/180; 536/28
[51] Int. Cl.$^2$ ................ A61K 37/00; A61K 45/02; A61K 45/04
[58] Field of Search .................. 260/112.5 R, 211.5, 260/231 CM, 211.5 R; 424/177, 180, 85

[56] References Cited

UNITED STATES PATENTS

| | | | |
|---|---|---|---|
| 2,851,453 | 9/1958 | Kennon | 424/180 |
| 3,066,075 | 11/1962 | Deutsch | 424/180 |
| 3,952,097 | 4/1976 | Levy | 260/112.5 R |

OTHER PUBLICATIONS

Matsuo et al., Bull. Chem. Soc. Japan, 39, 347–352 (1966).

*Primary Examiner*—Dolph H. Torrence

[57] ABSTRACT

A nuclease-resistant hydrophilic complex of polyriboinosinic-polyribocytidylic acid, poly-l-lysine and carboxymethylcellulose, and injectable preparations thereof in a pharmaceutically acceptable aqueous carrier such as saline solution. When administered to a primate host, the complex is effective in inducing the synthesis in such host of antiviral levels of interferon.

15 Claims, No Drawings

NUCLEASE-RESISTANT HYDROPHILIC COMPLEX OF POLYRIBOINOSINIC-POLYRIBOCYTIDYLIC ACID

This is a continuation-in-part of application Ser. No. 509,966, filed Sept. 27, 1974, now U.S. Pat. No. 3,952,097.

This invention relates to an interferon-inducing complex, and more particularly, to a nuclease-resistant hydrophilic complex of polyriboinosinic-polyribocytidylic acid useful for inducing the synthesis of interferon in primates.

The synthetic double-stranded RNA, polyriboinosinic-polyribocytidylic acid (hereinafter "In.Cn") is a known material known for its activity as an interferon inducer antiviral and antitumor agent in rodents. This material, the method for its preparation, and its aforementioned activity in rodents, are described, for example, by Field et al, *Proceedings of the National Academy of Sciences*, Volume 58, Pages 1004–1010 (1967), and Levy et al, *Proceedings of the National Academy of Sciences*, Volume 62, No. 2, pages 357–361 (1969). In man, however, In.Cn has proven to be a poor interferon inducer and has no detectable antitumor action. There is present in human serum a high level of hydrolytic activity against In.Cn which conceivably could be responsible for the low activity of the drug in man. Although several attempts have been made to prepare stabilized In.Cn derivatives, none of these compounds has proved to be fruitful. Moreover, previous attempts have been made to induce interferon in non-human primates with In.Cn, but little or no interferon was produced. While in man and non-human primates topical application has had some very minor success in prophylaxis of some virus disease, there has been no success in altering the course of systemic clinical disease with interferon inducers.

In connection with its activity in rodents, In.Cn of relatively low molecular weight, i.e., within the range from about $1 \times 10^5$ to about $3 \times 10^5$ daltons, has previously been found to have its activity enhanced by complexing it with high molecular weight poly-d-lysine, i.e., having a molecular weight of approximately 180,000. It was not possible, however, to use the same procedure with a high molecular weight In.Cn, i.e., having a molecular weight within the range of from about $7 \times 10^5$ to about $1 \times 10^7$ daltons, because intractable precipitates were produced. Further, since the amino acid, d-lysine, is not a natural occurring amino acid, it was felt that high molecular weight poly-d-lysine would very likely be restrictively antigenic.

It is therefore a basic object of the present invention to provide a hydrophilic complex of high molecular weight In.Cn which is relatively reistant to nuclease.

Another object of the invention is to provide a non-toxic and non-antigenic injectable preparation of a nuclease-resistant hydrophilic complex of high molecular weight In.Cn which, when administered in effective quantities to a primate host, is capable of inducing the synthesis of interferon in such host.

A further object of the invention is to provide an injectable preparation as described in the preceding object which, when administered in effective quantities to a primate host, is capable of inducing the synthesis of antiviral levels of interferon in such host.

The above and other objects are achieved in accordance with the present invention by providing a nuclease-resistant hydrophilic complex of high molecular weight In.Cn with relatively low molecular weight poly-l-lysine and carboxymethylcellulose. The In.Cn of the complex of the present invention has a molecular weight in the range of from about $7 \times 10^5$ to about $1 \times 10^7$ daltons, and the poly-l-lysine of such complex has a molecular weight within the range from about 2,000 to about 5,000.

Non-toxic and non-antigenic injectable preparations of the complex of the present invention are prepared by providing separate solutions of each of the three components of the complex in a pharmaceutically acceptable aqueous carrier such as pyrogen-free saline, and first mixing the poly-l-lysine solution with the carboxymethylcellulose solution, preferably by slowly pouring the former into the latter with stirring and continuing the stirring to redissolve any precipitate thereby formed. For best results, such stirring is preferably continued for a period of time sufficient to achieve minimum turbidity in the solution, which generally requires 2 to 3 days of stirring. To the resulting solution of poly-l-lysine-carboxymethylcellulose complex is then added the In.Cn solution, preferably followed by an additional 2 to 3 days of stirring, to form the final solution of In.Cn-poly-l-lysine-carboxymethylcellulose complex. The carboxymethylcellulose, which is a hydrophilic material negatively charged at neutral pH's, is an essential part of the complex, since without its presence, the In.Cn and the poly-l-lysine would form an intractable precipitate. Moreover, the above-described order of addition of the components of the complex, i.e., first forming the poly-l-lysine-carboxymethylcellulose complex and thereafter adding the In.Cn thereto to form the final In.Cn-poly-l-lysine-carboxymethylcellulose complex, is critical to the preparation of the complex since any other order of addition would result in the formation of an intractable precipitate.

While the In.Cn, poly-l-lysine, and carboxymethylcellulose may be used in a wide range of ratios in preparing nuclease-resistant hydrophilic In.Cn complexes, the injectable complex preparations in accordance with the present invention are preferably prepared so as to contain 1–4 mg/ml of the In.Cn, 0.75–3 mg/ml of the poly-l-lysine, and 0.25–1 percent by weight of the carboxymethylcellulose. A particularly suitable injectable preparation has been found to be a saline solution containing 2 mg/ml of In.Cn, 1.5 mg/ml of poly-l-lysine and 0.5 percent by weight of carboxymethylcellulose.

The In.Cn complexes of the present invention have been found to be four to ten times more resistant to hydrolysis by pancreatic ribonuclease and human serum than the parent uncomplexed In.Cn. When administered by injection to non-human primates such as monkeys or chimpanzees in dosages sufficient to provide from about 1 to about 5 mg of In.Cn per kg of body weight, and to humans in dosages sufficient to provide from about 0.5 to about 2 mg of In.Cn per kg of body weight, the complexes of the present invention are non/toxic and non-antigenic and will induce the synthesis of interferon in significant levels associated with antiviral effects. For example, when administered by injection in the above dosages, the In.Cn complexes of the present invention are effective in protecting primates, including, it is anticipated, humans, against such viral diseases as yellow fever virus, rabies, hepatitis and viral encephalitides; and in protecting non-human primates against Simian hemorrhagic fever virus. The preferred route of injection is either intravenously or intrathecally, with treatment preferably being given at a frequency of from every other day to daily in a dose sufficient to provide about 3 mg of In.Cn per kg of body weight in the case of non-human primates, and about 1 mg of In.Cn per kg of body weight in the case of humans.

The In.Cn complexes of the present invention are also expected to be effective for treating both humans and non-human primates, when administered by topical application, against various viral herpes diseases, such as herpetic keratoconjunctivitis (e.g., 1–2 drops in each eye every 6 hours of the above-described preparation of the complex), herpes virus of the genital organs, and cold sores; and when administered by inhalation, against various viral respiratory diseases, such as the common cold and influenza.

The following examples are given for purposes of illustrating the present invention. In the following examples, the In.Cn was prepared from an approximately equimolar mixture of polyriboinosinic acid and polyribocytidylic acid, both of which were purchased from P-L Biochemicals. Both of these materials were heterogeneous in size, with molecular weights in excess of $10^5$. They were dissolved at a concentration of 4 mg/ml in 0.85 percent NaCl. The solutions were warmed to 30° C and the polyribocytidylic acid was poured into the polyriboinosinic acid while constantly being mixed. There was a hypochromic shift of about 35 percent, indicating that the base-paired double-stranded structure had formed.

EXAMPLE I

The following solutions in pyrogen-free saline, 0.85 percent NaCl, were prepared: (1) 500 ml of In.Cn at 4 mg/ml; (2) 250 ml of 2 percent carboxymethylcellulose (7 HSP, high viscosity); and (3) 250 ml of poly-l-lysine (molecular weight 2,000) at 6 mg/ml. The poly-l-lysine solution was poured slowly into the carboxymethylcellulose solution with stirring. A precipitate was formed which redissolved after two additional days of stirring. The In.Cn solution was then poured into the solution of the poly-l-lysine-carboxymethylcellulose complex and stirred for an additional two days, to form a preparation of In.Cn-poly-l-lysine-carboxymethylcellulose complex. Such preparation contained 2 mg/ml of In.Cn, 1.5 mg/ml of poly-l-lysine, and 0,5 percent by weight of carboxymethylcellulose. As assayed by the rate of increase in optical density at 260 $m\mu$, the In.Cn complex so prepared was 4 to 10 times more resistant to hydrolysis by pancreatic ribonuclease and human serum than was the parent uncomplexed In.Cn.

EXAMPLE II

The preparation prepared in accordance with Example I was injected intravenously into four chimpanzees and 25 Rhesus monkeys in doses sufficient to provide 3 mg/kg of In.Cn. Representative serum interferon levels measured prior to the treatment and eight, twenty-four and forty-eight hours following the treatment are given in Table I, below.

| Time | Serum Interferon Levels (I.U./ml) Rhesus Monkey | Chimpanzee |
|---|---|---|
| Pretreatment | <10 | 10 |
| 8 hours | 125–6000 | 600 |
| 24 hours | 80–250 | 125 |
| 48 hours | 0–125 | 10 |

Comparable levels of interferon were found in cerebrospinal fluid when the preparation was injected intrathecally in chimpanzees and Rhesus monkeys. No overt toxicity was seen at these levels when the preparation was administered either intravenously or intrathecally.

EXAMPLE III

The preparation prepared in accordance with Example I was injected intravenously into four Rhesus monkeys in a dose sufficient to provide 3 mg/kg of In.Cn eight hours before an LD 100 challenge of Simian hemorrhagic fever virus, and the dose was repeated several times during the next two weeks. Hundreds of untreated Rhesus monkeys given the same challenge of the virus were all dead in seven to eight days. Of the four treated monkeys, three of them developed no disease. The fourth monkey developed the disease two weeks later, but this disappeared on additional treatment. This experiment demonstrates that the preparation of the present invention is capable of inducing the synthesis of interferon in primates at levels sufficient to control systemic virus disease.

An analogous protocol was followed using yellow fever virus, rabies, hepatitis, and viral encephalitides in place of the Simian hemorrhagic fever virus, with comparable results.

An analogous protocol is followed in treating humans against yellow fever virus, rabies, hepatitis, and viral encephalitides, but with the dosage of the preparation of Example I reduced to one sufficient to provide approximately 1 mg/kg of In.Cn.

The embodiments of the invention in which an exclusive property or privilege is claimed are defined as follows:

1. A nuclease-resistant hydrophilic complex of relatively high molecular weight polyriboinosinic-polyribocytidylic acid, relatively low molecular weight poly-l-lysine and carboxymethylcellulose.

2. The complex of claim 1 wherein said polyriboinosinic-polyribocytidylic acid has a molecular weight in the range of from about $7\times10^5$ to about $10^7$ daltons.

3. The complex of claim 1 wherein said poly-l-lysine has a molecular weight in the range of from about 2,000 to about 5,000.

4. A method of preparing a nuclease-resistant hydrophilic complex of relatively high molecular weight polyriboinosinic-polyribocytidylic acid, relatively low molecular weight poly-l-lysine and carboxymethylcellulose, which comprises the steps of first mixing an aqueous solution of relatively low molecular weight poly-l-lysine with an aqueous solution of carboxymethylcellulose with stirring to thereby form a poly-l-lysine-carboxymethylcellulose intermediate complex, and thereafter adding to the resulting aqueous solution of said intermediate complex an aqueous solution of relatively high molecular weight polyriboinosinic-polyribocytidylic acid with stirring to thereby form the polyriboinosinic-polyribocytidylic acid-poly-l-lysine-carboxymethylcellulose final complex.

5. The method of claim 4 wherein said intermediate complex is formed by slowly pouring said aqueous solution of poly-l-lysine into said aqueous solution of carboxymethylcellulose with stirring, and continuing said stirring for a period of time sufficient to achieve minimum turbidity in the resulting aqueous solution.

6. The method of claim 5 wherein the stirring of said aqueous solution of poly-l-lysine with said aqueous solution of carboxymethylcellulose is carried out for a period of approximately 2 to 3 days.

7. The method of claim 5 wherein the stirring of said aqueous solution of said intermediate complex with said aqueous solution of polyriboinosinic-polyribocytidylic acid is carried out for a period of approximately 2 to 3 days.

8. The method of claim 4 wherein the concentrations of said polyriboinosinic-polyribocytidylic acid, said poly-l-lysine and said carboxymethylcellulose in the respective starting aqueous solutions thereof and the relative proportions of said starting aqueous solutions are selected so as to provide in the resulting aqueous solution of said final complex 1–4 mg/ml of said polyriboinosinic-polyribocytidylic acid, 0.75–3 mg/ml of said poly-l-lysine, and 0.25–1% by weight of said carboxymethylcellulose.

9. The method of claim 8 wherein said starting aqueous solutions are all saline solutions.

10. The method of claim 9 wherein the concentrations of said polyriboinosinic-polyribocytidylic acid, said poly-l-lysine and said carboxymethylcellulose in the respective starting saline solutions thereof and the relative proportions of said starting saline solutions are selected so as to provide in the resulting saline solution of said final complex 2 mg/ml of said polyriboinosinic-polyribocytidylic acid, 1.5 mg/ml of said poly-l-lysine, and 0.5% by weight of said carboxymethylcellulose.

11. A method of inducing the synthesis of interferon in a primate which comprises administering to a primate host a nuclease-resistant hydrophilic complex of relatively high molecular weight polyriboinosinic-polyribocytidylic acid, relatively low molecular weight poly-l-lysine and carboxymethylcellulose in a dose sufficient to provide an interferon-inducing amount of said polyriboinosinic-polyribocytidylic acid.

12. The method of claim 11 wherein said host is a non-human primate and said complex is administered from every other day to daily in a dose sufficient to provide from about 1 to about 5 mg of said polyriboinosinic-polyribocytidylic acid per kg of body weight.

13. The method of claim 12 wherein said complex is administered from every other day to daily in a dose sufficient to provide about 3 mg of said polyriboinosinic-polyribocytidylic acid per kg of body weight.

14. The method of claim 11 wherein said host is a human and said complex is administered from every other day to daily in a dose sufficient to provide from about 0.5 to about 2 mg of said polyriboinosinic-polyribocytidylic acid per kg of body weight.

15. The method of claim 14 wherein said complex is administered from every other day to daily in a dose sufficient to provide about 1 mg of said polyriboinosinic-polyribocytidylic acid per kg of body weight.

* * * * *